United States Patent [19]

Hatayama et al.

[11] Patent Number: 4,557,871
[45] Date of Patent: Dec. 10, 1985

[54] NOVEL STYRENE DERIVATIVES OF THE GENERAL FORMULA

[75] Inventors: Katsuo Hatayama, Ohmiya; Kensei Yoshikawa, Saitama; Tatsuhiko Sano, Ohmiya; Yutaka Ohuchi, Ohimya; Tomomi Ota, Ohimya; Kazuto Sekiuchi, Tokyo; Kaoru Sota, Tokorozawa, all of Japan

[73] Assignee: Taisho Pharmaceutical Co., Ltd., Shizuoka, Japan

[21] Appl. No.: 609,858

[22] Filed: May 14, 1984

[30] Foreign Application Priority Data

May 19, 1983 [JP] Japan .................................. 58-87951

[51] Int. Cl.$^4$ .......................... C07F 5/06; C07C 63/64
[52] U.S. Cl. .................................... 556/183; 544/164; 544/404; 546/297; 548/190; 560/30; 560/41; 560/104; 562/495; 564/182; 568/308; 568/812; 260/465 R
[58] Field of Search ...................... 260/448 R, 465 R; 514/532, 570; 544/164, 404; 546/297; 548/190; 560/30, 41, 104; 562/495; 564/182; 568/302, 812

[56] References Cited

U.S. PATENT DOCUMENTS 3,385,886   5/1968   Nicholson et al. ................... 562/495

Primary Examiner—Paul J. Killos
Attorney, Agent, or Firm—Pahl, Lorusso & Loud

[57] ABSTRACT

Novel styrene derivatives of the general formula

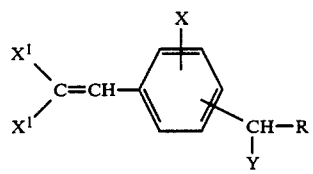

wherein X is hydrogen or halogen, $X^1$ is halogen, R is hydrogen or methyl, Y is hydroxymethyl, carboxyl, —$COOR^1$ or —$COR^2$ wherein $R^1$ is prenyl, geranyl, farnesyl, cyclohexyl, phthalidyl, straight or branched chain alkyl having 1 to 6 carbon atoms, or said alkyl substituted with hydroxy, methoxy, pyridyl or alkanoyloxy having 2 to 16 carbon atoms, and $R^2$ is amino, hydroxyamino mono-(or di-)alkylamino in which the alkyl moiety contains 1 or 2 carbon atoms, ethoxycarbonylmethylamino, carboxymethylamino, thiazolylamino, cyclohexylamino, pyridylamino, morpholino, N-methylpiperazino, phenylamino, phenylamino substituted with one or two of halogen, hydroxy, methyl, methoxy, trifluoromethyl or carboxyl at the phenyl ring, and the pharmaceutically acceptable salts thereof when Y is carboxyl are disclosed. These compounds exhibit high and long-lasting anti-inflammatory, analgesic and anti-pyretic activity.

6 Claims, No Drawings

NOVEL STYRENE DERIVATIVES OF THE GENERAL FORMULA

The present invention relates to novel styrene derivatives which have high and long-lasting anti-inflammatory, analgesic and anti-pyretic activity when compared with known analogous compounds. In particular, the structures of the compounds of the present invention are characterized by having a dihalogenovinyl group at the phenyl ring.

The compounds of the present invention are represented by the general formula

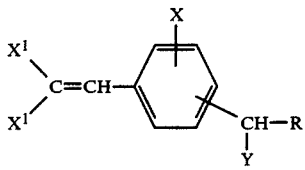

wherein X is hydrogen or halogen, $X^1$ is halogen, R is hydrogen or methyl, Y is hydroxymethyl, carboxyl, —$COOR^1$ or —$COR^2$ wherein $R^1$ is straight or branched chain alkyl having 1 to 6 carbon atoms, the alkyl substituted with hydroxy, methoxy, pyridyl or alkanoyloxy having 2 to 16 carbon atoms, prenyl, geranyl, farnesyl, cyclohexyl or phthalidyl, and $R^2$ is amino, hydroxyamino mono-(or di-)alkylamino in which the alkyl moiety contains 1 or 2 carbon atoms, ethoxycarbonylmethylamino, carboxymethylamino, phenylamino, phenylamino substituted with one or two of halogen, hydroxy, methyl, methoxy, trifluoromethyl or carboxyl at the phenyl ring, thiazolylamino, cyclohexylamino, pyridylamino, morpholino or N-methylpiperazino, and the pharmaceutically acceptable salts thereof when Y is carboxyl.

The terms "halogen" is the definitions of X, $X^1$, $R^2$ and $X^3$ and "halogeno" in dihalogenoethylene as used throughout in the specification and claims refer to fluorine, chlorine and bromine.

Preferred compounds of the present invention are the compounds of formula I wherein X is hydrogen or halogen, $X^1$ is chlorine, R is methyl and Y is carboxyl, carboxyamino or hydroxymethyl. Most preferred compounds of the present invention are the compounds of formula I wherein X is hydrogen, $X^1$ is chlorine, R is methyl and Y is carboxyl, —CH(R)Y is at the 4-position of the styrene.

The compounds of the formula I may be prepared, for example, by the following methods.

A compound of the general formula

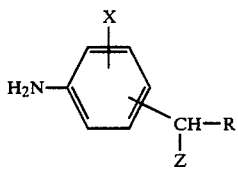

wherein R and X are as defined above and Z is carboxyl, is converted into its diazonium salt by a conventional manner, the resulting diazonium salt is reacted with a 1,1-dihalogenoethylene in the presence of a buffer and cupric chloride in an organic solvent to give a compound of the general formula

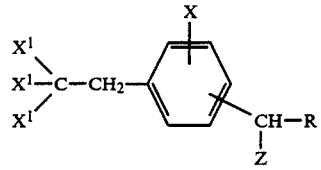

wherein R, X, $X^1$ and Z are as defined above, and then the compound of formula III is treated with a base in an organic solvent to give a compound of formula I wherein Y is carboxyl.

Examples of the buffer used in the reaction of the diazonium salt with dihalogenoethylene are sodium carbonate, calcium hydroxide, magnesium hydroxide, sodium acetate and the like.

Examples of the organic solvent used in the reaction of the diazonium salt with dihalogenoethylene are acetone, acetonitrile, dimethylsulfoxide, pyridine, N-methylpyrrolidone and the like.

The temperature at which the compound of formula III is treated with the base is not particularly critical, but the temperatures from about 25° to 100° C. are generally satisfactory.

Examples of bases useful for treating the compound of formula III are anhydrous potassium carbonate, anhydrous sodium carbonate, potassium hydroxide, sodium hydroxide, 1,5-diazabicyclo[5.4.0]undec-5-ene and the like.

Examples of organic solvents useful for treating the compound of formula III are benzene, dimethylformamide, dimethylsulfoxide, methanol, ethanol, acetone and the like.

The compound of formula I wherein Y is other than carboxyl can be prepared from the compound of formula I wherein Y is carboxyl.

That is, in order to the compound of formula I wherein Y is —$COOR^1$ ($R^1$ is defined above), the compound of formula I wherein Y is carboxyl is reacted (1) with $X^2$-$R^1$ ($R^1$ is as defined above, and $X^2$ is chlorine, bromine or iodine) in the presence of a base such as sodium carbonate, potassium carbonate, sodium hydroxide, potassium hydroxide and the like in an organic solvent such as acetone, benzene, dimethylformamide and the like, (2) with HO-$R^1$ ($R^1$ is as defined above) in the presence of an acid such as sulfuric acid or hydrochloric acid, or a condensing agent such as dicyclohexylcarbodiimide, or (3) with chlorinating agent such as thionyl chloride or oxalyl chloride in an organic solvent such as benzene, chloroform and the like to give the corresponding acid chloride, which is then reacted with HO$R^1$ ($R^1$ is as defined above) in the the presence of a basic condensing agent such as pyridine, triethylamine, alkali metal carbonate or alkali metal hydroxide in an organic solvent such as benzene to obtain the compound of formula I wherein Y is —$COOR^1$ ($R^1$ is as defined above).

The compound of formula I wherein Y is —$COR^2$ ($R^2$ is as defined above) can be prepared by a method which comprises converting the compound of formula I wherein Y is carboxyl into the corresponding acid chloride by a procedure similar to that of the above, and then reacting the acid chloride with $HR^2$ ($R^2$ is as defined above) in the presence of a base such as pyridine, methylmorpholine or triethylamine in an organic solvent such as benzene, acetone, chloroform and the like.

The compound of formula I wherein Y is hydroxymethyl can be obtained by reducing the compound of formula I wherein Y is carboxyl or —COOR$^1$ (R$^1$ is as defined above) with a reductant such as lithium aluminum hydride, diisobutyl aluminum hydride or the like.

The compound of formula I wherein Y is —COR$^2$ (R$^2$ is defined above) can also be prepared by reaction of the compound of formula I wherein Y is —COOR$^1$ (R$^1$ is as defined above) with HR$^2$ (R$^2$ is as defined above).

Alternatively, the compound of formula I wherein Y is —COOR$^1$ (R$^1$ is as defined above) can be prepared by reacting a compound of the general formula

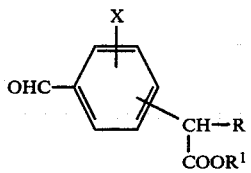
IV wherein X, R and R$^1$ are as defined above with a halomethylating agent such as carbon tetrachloride, bromotrichloromethane, sodium chlorodifluoroacetate, dibromidifluoromethane, difluoromethane or the like in the presence of triphenylphosphine, hexamethylphosphorous triamide in an organic solvent such as diglyme, triglyme, chloroform, dichloromethane, tetrahydrofuran and the like.

The compound of formula I wherein Y is —COOR$^1$ (R$^1$ is as defined above) can be converted into the the compound of formula I wherein y is carboxyl by hydrolysis.

The pharmaceutically acceptable salts of the compounds of formula I wherein Y is carboxyl may be prepared by conventional techniques, for example, by treating the compound of formula I wherein Y is carboxyl with inorganic or organic bases such as sodium hydroxide, calcium chloride, magnesium chloride, zinc chloride, aluminum chloride, aminopyridine, morpholine, lysine, arginine, ethanolamine, aminopropanol and the like in a suitable solvent.

Purification of the compounds of formula I, if necessary or if desired, may be carried out by conventional techniques such as distillation, recrystallization and/or silica gel column chromatography.

The compound of formula II are generally known, but if a specific compound is not known it may be conveniently prepared, for example, by the following known methods. The compound of the general formula

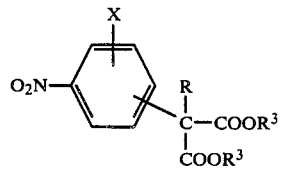
V wherein R and X are as defined above and R$^3$ is alkyl having 1 to 6 carbon atoms, is subjected to hydrolysis, decarboxylation and reduction of the nitro group by conventional techniques to give the compound of formula II.

Alternatively, the compound of the general formula

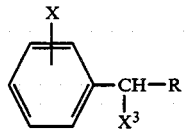
VI wherein X and R are as defined above and X$^3$ is halogen can be subjected to cyanation, nitration, hydrolysis for converting cyano into carboxyl, and reduction for converting nitro into amino by conventional techniques to give the compound of formula II.

As stated above, the compounds of the present invention have high and long-lasting anti-inflammatory and analgesic and anti-pyretic activity. For these purposes, a compound of the present invention may be administered orally in a conventional dosage form such as tablet, capsule or powder prepared according to conventional pharmaceutical practices with pharmaceutically acceptable carriers. A single dose provided on a basis of about 0.2-5 mg/kg/day is appropriate. These compounds may be also administered topically in the range of 0.01 to 10.0% by weight in a conventional cream, ointment or lotion.

TEST EXAMPLE 1

Anti-inflammatory activity was evaluated by the Winter's method [Journal of Pharmacology and Experimental Therapeutics, volume 141, page 369(1963)]. Male Wistar rats (group of 6 animals) were administered orally the test compounds (dose: 6 mg/kg) one hour before inducing the edema in left hind paw with 0.1 ml of a 1% carrageenin-saline suspension. Volumes of the hind paws were determined with a volume meter 3 hours after the injection of carrageenin. Indomethacin (Control 1) and 4-vinylphenylacetic acid (Control 2) were used as controls.

The results are given in the following Table.

TABLE 1

| Test Compound | Inhibition of edema (%) | Test Compound | Inhibition of edema (%) |
|---|---|---|---|
| ST-1 | 66.1 | ST-36 | 43.0 |
| ST-7 | 48.4 | ST-38 | 35.6 |
| ST-8 | 64.8 | ST-39 | 51.4 |
| ST-10 | 62.4 | ST-41 | 48.8 |
| ST-37 | 63.1 | ST-42 | 60.4 |
| Control 1 | 68.2 | ST-43 | 37.1 |
| ST-2 | 63.9 | ST-44 | 59.8 |
| ST-3 | 31.9 | ST-45 | 44.8 |
| ST-4 | 32.0 | ST-46 | 32.2 |
| ST-5 | 46.5 | ST-47 | 49.9 |
| ST-9 | 58.0 | ST-48 | 32.7 |
| ST-11 | 26.5 | ST-49 | 53.3 |
| ST-14 | 33.6 | ST-50 | 61.4 |
| ST-16 | 43.1 | ST-55 | 38.2 |
| ST-17 | 40.0 | ST-56 | 39.4 |
| ST-20 | 47.0 | ST-58 | 39.0 |
| ST-22 | 35.5 | ST-59 | 57.3 |
| ST-23 | 35.5 | ST-60 | 50.8 |
| ST-24 | 30.0 | ST-61 | 43.7 |
| ST-25 | 37.1 | ST-62 | 43.2 |
| ST-34 | 32.5 | Control 1 | 59.3 |
| ST-35 | 46.0 | Control 2 | 15.7 |

Note: The compound numbers in Table 1 are as defined in Examples as described hereinafter.

TEST EXAMPLE 2

Following a procedure similar to that of Test example 1, the test compounds were administered orally to the rats 1, 24 or 48 hours before inducing the edema, and and there was obtained a result shown in Table 2.

TABLE 2

| Test compound | dose (mg/kg) | Inhibition of edema (%) | | |
|---|---|---|---|---|
| | | 1 hr | 24 hrs | 48 hrs |
| ST-1 | 1.5 | 42.6 | 31.1 | 25.3 |
| Control 3 | 1.5 | 48.6 | 13.3 | 2.1 |
| Control 1 | 3 | 30.4 | 8.1 | 0.8 |
| Control 4 | 6 | 59.3 | −8.5 | 3.7 |
| Control 2 | 30 | 40.2 | 1.3 | −3.5 |

Note: ST-1, Controls 1 and 2 are as defined above, and Controls 3 and 4 are piroxicam and 2-[4-(2,2-dimethylvinyl)phenyl]propionic acid, respectively.

The present invention is further illustrated by the following examples.

EXAMPLE 1

(1) Thirty milliliters of water and 30 ml of conc. hydrochloric acid were added to 20 g of 2-(4-aminophenyl)propionic acid to form the hydrochloride salt, to which 20 ml of an aqueous solution of 9 g of sodium nitrite was added dropwise at −10° C. To the mixture was added dropwise 200 ml of acetone, and there were added successively 40 g of 1,1-dichloroethylene, 10 g of sodium hydrogen carbonate and 2 g of cupric chloride dihydrate at −5° C. The mixture was stirred for 7 hours while warming gradually up to room temperature. The reaction mixture was separated into two layers. The upper layer was concentrated, ice-water was added, and the mixture was extracted with ether. The ether layer was washed with water, dried over anhydrous sodium sulfate and concentrated to obtain crude crystals, which were subjected to silica gel column chromatography (eluent: n-hexane—ethyl acetate=4:1) and then recrystallized from n-hexane-benzene to obtain 15.8 g of 2-[4-(2,2,2,-trichloroethyl)phenyl]propionic acid, m.p. 110°–112° C.

(2) To 140 ml of dimethylformamide were added 8.6 g of 2-[4-(2,2,2-trichloroethyl)phenyl]propionic acid and 10.5 g of anhydrous potassium carbonate, followed by stirring at 75° C. for 3 hours. The mixture was cooled, ice-water was added, and the mixture was washed with n-hexane. The aqueous layer was made acidic with hydrochloric acid and extracted with n-hexane. The n-hexane layer was washed with water, dried over anhydrous sodium sulfate and concentrated to obtain crude crystals, which were recrystallized from n-hexane to obtain 5.1 g of 2-[4-(2,2-dichlorovinyl)phenyl]propionic acid(ST-1), m.p. 48°–50° C.

The following compounds were obtained from the corresponding materials by procedures similar to that of Example 1.

4-(2,2-Dichlorovinyl)phenylacetic acid(ST-2), m.p. 96°–98° C.

3-(2,2-Dichlorovinyl)phenylacetic acid (ST-3), m.p. 85.5°–86.5° C.

2-[3-(2,2-Dichlorovinyl)phenyl]propionic acid(ST-4) as an oily substance.

EXAMPLE 2

(1) In 260 ml of carbon tetrachloride were dissolved 60 g of ethyl 2-(4-formylphenyl)propionate and 122 g of triphenylphosphine, followed by stirring in a stream of nitrogen gas at 50° C. for 4.5 hours. After cooling, the mixture was poured into 1 l of cold n-hexane and filtered. The filtrate was concentrated under reduced pressure to give an oily substance, which was subjected to silica gel column chromatography (eluent: n-hexane—ethyl acetate=40:1) to obtain 29 g of ethyl 2-[4-(2,2-dichlorovinyl)phenyl]propionate (ST-5) as an oily substance, b.p.$_{0.2-0.3}$ 128°–129° C.

(2) To 40 ml of a 50% aqueous methanol solution were added 2.1 g of ethyl 2-[4-(2,2-dichlorovinyl)phenyl]propionate(ST-5) and 2.0 g of anhydrous potassium carbonate, followed by stirring at 55° C. for 8 hours. Methanol was evaporated off under reduced pressure and water was added. The mixture was made acidic with hydrochloric acid and extracted with ether. The ether layer was washed successively with water and a saturated brine, dried over anhydrous magnesium sulfate and the solvent was evaporated off to give crude crystals, which were recrystallized from n-hexane to obtain 1.5 g of 2-[4-(2,2-dichlorovinyl)phenyl]propionic acid(ST-1), m.p. 48°–50° C.

EXAMPLE 3

(1) In 5 ml of diglyme were dissolved 6 g of ethyl 2-(4-formylphenyl)propionate and 6.36 g of triphenylphosphine. The solution was heated at 130°–140° C. and 15 ml of a diglyme solution of 5.54 g of sodium chlorodifluoroacetate was added dropwise with stirring. The mixture was stirred for further 2 hours, cooled and filtered through Celite. The filtrate was subjected to silica gel column chromatography (eluent: n-hexane—ethyl acetate=19:1) to afford 3.56 g of ethyl 2-[4-(2,2-difluorovinyl)phenyl]propionate(ST-6) as an oily substance.

IR (neat) cm$^{-1}$: 1730 ($CO_2C_2H_5$, $CF_2$=CH).

NMR (CDCl$_3$)

$\delta$=1.22 (3H, t, J=7.0 HZ, CH$_2$C$\underline{H}_3$); 1.50 (3H, d, J=7.6 HZ, >CHC$\underline{H}_3$); 3.70 (1H, q, J=7.6 HZ, Ar-C$\underline{H}$); 4.14 (2H, q, J=7.0 Hz, —C$\underline{H}_2$CH$_3$); 5.25 (1H, d.d, J=4 Hz, 26 Hz, CF$_2$=C$\underline{H}$—); 7.30 (4H, s, Ar-H×4).

(2) To 60 ml of a 5% aqueous methanol solution were added 2.57 g of ethyl 2-[4-(2,2-difluorovinyl)phenyl]propionate(ST-6) and 5.9 g of anhydrous potassium carbonate, followed by stirring at 50° C. for 5 hours. To this was added water, and the mixture was made acidic with hydrochloric acid and extracted with ether. The ether layer was washed with water and dried over anhydrous sodium sulfate and the solvent was evaporated off. The residue thus obtained was subjected to silica gel column chromatography (eluent: n-hexane—ethyl acetate=14:1) to give 1.5 g of 2-[4-(2,2-difluorovinyl)phenyl]propionic acid(ST-7) as an oily substance.

IR (neat) cm$^{-1}$: 1725 (CF$_2$=CH), 1705 (CO$_2$H)

NMR (CDCl$_3$)

$\delta$=1.49 (3H, d, J=8.0 Hz, >CHC$\underline{H}_3$); 3.72 (1H, q, J=8.0 Hz, Ar-C$\underline{H}$); 5.26 (1H, d.d, J=4 Hz, 26 Hz, CF$_2$=C$\underline{H}$—); 7.30 (4H, s, Ar-H×4) 11.40 (1H, br. s, OH).

EXAMPLE 4

(1) To 30 g of diethyl (3-fluoro-4-nitrophenyl)methylmalonate was added 250 ml of a 47% hydrobromic acid solution, followed by reflux for 7 hours. The mixture was cooled, ice-water was added, and the mixture was extracted with ether. The ether layer was washed with water and dried over anhydrous magnesium sulfate and the solvent was evaporated off. The crude crystals thus obtained were recrystallized from ethyl acetate—n-hexane to give 17.7 g of 2-(3-fluoro-4-nitrophenyl)propionic acid, m.p. 74°–77° C.

(2) In 100 ml of ethanol was dissolved 3 g of 2-(3-fluoro-4-nitrophenyl)propionic acid. To the solution was added 0.25 g of 5% palladium on charcoal to conduct catalytic hydrogenation. The catalyst was filtered off and the solvent was evaporated off under reduced pressure to afford 2.55 g of 2-(4-amino-3-fluorophenyl)propionic acid as an oily substance.

IR (nujol) cm$^{-1}$: 3350, 3270 (NH$_2$), 1680(COOH).
NMR (CDCl$_3$).
$\delta = 1.45$ (3H, d, J=7 Hz, —CH$_3$);
3.62 (1H, q, J=7 Hz, >CHCH$_3$); 6.46 (3H, br. s, NH$_2$, OH); 6.68–6.84 (1H, m, $\overline{Ar}$-H); 6.84–7.08 (2H, m, Ar-H×2).

(3) In 10 ml of a 17% aqueous hydrochloric acid solution was dissolved 2.5 g of 2-(4-amino-3-fluorophenyl)propionic acid. To the solution was added dropwise 5 ml of an aqueous solution of 1.04 g of sodium nitrite at −15° C.−−10° C. with stirring, and the reaction was carried out for an hour. To the mixture were added 25 ml of acetone and 3 g of 1,1-dichloroethylene at −10° C.−−5° C., followed by 2.5 g of sodium hydrogen carbonate and 0.5 g of cupric chloride dihydrate. The mixture was gradually warmed up to room temperature and stirred at room temperature for 2 hours. Acetone was evaporated off and the residue was extracted with ether. The ether layer was washed with water and dried over anhydrous magnesium sulfate and the solvent was evaporated off. The residue thus obtained was subjected to silica gel column chromatography (eluent: ethyl acetate—dioxane—n-hexane=1:1:4) and recrystallized from n-hexane to obtain 2.3 g of 2-[3-fluoro-4-(2,2,2-trichloroethyl)phenyl]propionic acid, m.p. 92°–94° C.

(4) In 30 ml of dimethylformamide was dissolved 2.0 g of 2-[3-fluoro-4-(2,2,2-trichloroethyl)phenyl]propionic acid, and 2.46 g of anhydrous potassium carbonate was added. The mixture was stirred at 75°–80° C. for 3 hours, and cooled. Ice-water was added, and the mixture was made acidic with hydrochloric acid and extracted with n-hexane. The n-hexane layer was washed with water and dried over anhydrous magnesium sulfate and the solvent was evaporated off. The residue thus obtained was subjected to silica gel column chromatography (eluent: ethyl acetate—dioxane—n-hexane=1:1:4) to give 1.28 g of 2-[4-(2,2-dichlorovinyl)-3-fluorophenyl]propionic acid(ST-8) as an oily substance.

IR (neat) cm$^{-1}$: 1710 (COOH).
NMR (CDCl$_3$).
$\delta = 1.52$ (3H, d, J=7 Hz, CH$_3$); 3.75 (1H, q, J=7 Hz, >CHCH$_3$); 6.96 (1H, s, Ar-CH); 7.03–7.20 (2H, m, Ar-$\overline{H}$×2); 7.72–7.86 (1H, m, Ar-$\overline{H}$).

The following compound was obtained from the corresponding material by a procedure similar to that of Example 4.

2-[3-Chloro-4-(2,2-dichlorovinyl)phenyl]propionic acid (ST-9), m.p. 66°–67° C.

EXAMPLE 5

In 100 ml of ether was dissolved 2 g of ethyl 2-[4-(2,2-dichlorovinyl)phenyl]propionate(ST-5), followed by cooling at −65° C. To this was added 281 mg of lithium aluminum hydride portionwise, followed by stirring for an hour. A small amount of water was added and the mixture was filtered. The filtrate was concentrated under reduced pressure and the residue thus obtained was subjected to silica gel column chromatography (eluent: n-hexane—ethyl acetate=14:1) to afford 1.38 g of 2-[4-(2,2-dichlorovinyl)phenyl]propanol(ST-10) as an oily substance.

IR (neat) cm$^{-1}$: 3300 (OH).
NMR (CDCl$_3$).
$\delta = 1.28$ (3H, d, J=6.8 Hz, >CHCH$_3$); 1.43 (1H, s, OH); 2.97 (1H, m, >CHCH$_3$); 3.71 (2H, d, J=6.0 Hz, —CH$_2$OH); 6.85 (1H, s, Cl$_2$C=CH—); 7.26 (2H, d, J=8.0 Hz, Ar-H×2); 7.53 (2H, d, J=8.0 Hz, Ar-H×2).

EXAMPLE 6

In 20 ml of benzene were dissolved 1 g of 2-[4-(2,2-dichlorovinyl)phenyl]propionic acid(ST-1) and 0.55 g of pyridine. To the solution was added dropwise 0.8 g of thionyl chloride with ice-cooling and stirring, and the stirring was carried out for an hour and then at room temperature for another 2 hours. The reaction mixture was diluted with n-hexane, washed successively with cold water and a cold saturated brine, and then dried over anhydrous magnesium sulfate. The solvent was evaporated off and the residue was dissolved in 5 ml of benzene, and added dropwise to a 28% aqueous ammonia solution with ice-cooling and stirring. The mixture was stirred at that temperature for 2 hours and further at room temperature overnight. The crude crystals precipitated were collected on a filter and recrystallized from n-hexane—ethyl acetate to give 0.7 g of 2-[4-(2,2-dichlorovinyl)phenyl]propionamide(ST-11), m.p. 108°–109° C.

The following compounds were obtained from the corresponding materials by procedures similar to that of Example 6.

N-Phenyl-2-[4-(2,2-dichlorovinyl)phenyl]propionamide (ST-12), m.p. 157°–158° C.

N-(4-Hydroxyphenyl)-2-[4-(2,2-dichlorovinyl)phenyl]propionamide (ST-13), m.p. 185°–186° C.

N-(4-Methylphenyl)-2-[4-(2,2-dichlorovinyl)phenyl]propionamide (ST-14), m.p. 114.5°–115.5° C.

N-(4-Methoxyphenyl)-2-[4-(2,2-dichlorovinyl)phenyl]propionamide (ST-15), m.p. 127.5°–129° C.

N-(4-Chlorophenyl)-2-[4-(2,2-dichlorovinyl)phenyl]propionamide (ST-16), m.p. 150.5°–151.5° C.

N-(4-Fluorophenyl)-2-[4-(2,2-dichlorovinyl)phenyl]propionamide (ST-17), m.p. 133°–134.5° C.

N-(2-Fluorophenyl)-2-[4-(2,2-dichlorovinyl)phenyl]propionamide (ST-18), m.p. 123°–124° C.

N-(2,4-Difluorophenyl)-2-[4-(2,2-dichlorovinyl)phenyl]propionamide (ST-19), m.p. 120°–121° C.

4-{2-[4-(2,2-Dichlorovinyl)phenyl]propionylamino}benzoic acid(ST-20), m.p. 157°–158° C.

N-(3-Trifluoromethylphenyl)-2-[4-(2,2-dichlorovinyl)phenyl]propionamide(ST-21), m.p. 115°–115.5° C.

N-(2-Pyridyl)-2-[4-(2,2-dichlorovinyl)phenyl]propionamide (ST-22), m.p. 132.5°–133.5° C.

N-{2-[4-(2,2-Dichlorovinyl)phenyl]propionyl}glycine ethyl ester(ST-23), m.p. 82°–83° C.

N-{2-[4-(2,2-Dichlorovinyl)phenyl]propionyl}glycine(ST-24), m.p. 133°–134° C.

N-Ethyl-2-[4-(2,2-dichlorovinyl)phenyl]propionamide(ST-25), m.p. 94°–95° C.

N,N-Diethyl-2-[4-(2,2-dichlorovinyl)phenyl]propionamide (ST-26), b.p. 156°–157° C./0.3 mmHg.

N-Cyclohexyl-2-[4-(2,2-dichlorovinyl)phenyl]propionamide (ST-27), m.p. 153°–154° C.

N-(2-Thiazolyl)-2-[4-(2,2-dichlorovinyl)phenyl]propionamide (ST-28), m.p. 177°–178° C.

N-{2-[4-(2,2-Dichlorovinyl)phenyl]propionyl}morpholine (ST-29), b.p. 173°–176° C./0.22 mmHg.

N-{2-[4-(2,2-Dichlorovinyl)phenyl]propionyl}-N'-methylpiperazine(ST-30), b.p. 175°–178° C./0.27 mmHg.

N-(4-Chlorophenyl)-3-(2,2-dichlorovinyl)-phenylacetoamide (ST-31), m.p. 118.5°–120.5° C.

N-Cyclohexyl-3-(2,2-dichlorovinyl)-phenylacetoamide(ST-32), m.p. 105°–106° C.

N-(2-Thiazolyl)-3-(2,2-dichlorovinyl)phenylacetoamide (ST-33), m.p. 143°–144.5° C.

EXAMPLE 7

In 1.5 ml of methanol was dissolved 1 g of ethyl 2-[4-(2,2-dichlorovinyl)phenyl]propionate(ST-5). To this were added 20 ml of a 80% aqueous methanol solution of hydroxylamine prepared previously from 1.5 g of hydroxylamine hydrochloride and 1.3 g of sodium hydroxide, followed by stirring at room temperature for 4 hours.

The reaction mixture was concentrated to one-third of its volume under reduced pressure and water was added. The crude crystals thus precipitated were collected on a filter and 2N hydrochloric acid was added. The crude crystals thus obtained were recrystallized from n-hexane—ethyl acetate to afford 0.43 g of 2-[4-(2,2-dichlorovinyl)phenyl]propionylhydroxamic acid(ST-34), m.p. 120°–121° C.

EXAMPLE 8

In 2 ml of methanol was dissolved 1 g of 2-[4-(2,2-dichlorovinyl)phenyl]propionic acid(ST-1). The solution was adjusted to pH 9 by addition of a 5% aqueous sodium hydroxide solution with stirring. Methanol was evaporated off under reduced pressure and the crude crystals thus obtained were recrystallized from ethyl acetate to afford 1 g of sodium 2-[4-(2,2-dichlorovinyl)phenyl]propionate(ST-35), m.p. 171°–175° C.

EXAMPLE 9

In 2 ml of methanol was dissolved 1 g of 2-[4-(2,2-dichlorovinyl)phenyl]propionic acid(ST-1). The solution was adjusted to pH 9 by addition of a 5% aqueous sodium hydroxide solution with stirring. To the solution was added dropwise a 5% aqueous calcium chloride solution with stirring. The crude crystals precipitated were collected on a filter and recrystallized from ethyl acetate to obtain 0.8 g of calcium 2-[4-(2,2-dichlorovinyl)phenyl]propionate(ST-36), m.p. over 243° C. (with decomposition).

The following compound was obtained from the corresponding material by a procedure similar to that of Example 9.

Aluminum 2-[4-(2,2-dichlorovinyl)phenyl]propionate(ST-37), m.p. over 254° C. (with decomposition).

EXAMPLE 10

In 15 ml of ether was dissolved 1 g of 2-[4-(2,2-dichlorovinyl)phenyl]propionic acid(ST-1), and 3 ml of an ether solution of 350 mg of morpholine was added dropwise with stirring. The crude crystals thus precipitated were recrystallized from n-hexane—ethyl acetate to give 1.1 g of morpholinium 2-[4-(2,2-dichlorovinyl)phenyl]propionate(ST-38), m.p. 104°–105° C.

The following compound was obtained from the corresponding material by a procedure similar to that of Example 10.

2-Pyridylammonium 2-[4-(2,2-dichlorovinyl)phenyl]propionate(ST-39), m.p. 80°–81° C.

EXAMPLE 11

(1) In 300 ml of dimethyl sulfoxide was dissolved 35 g of sodium cyanide by heating at 90° C., and 45 g of 2-fluoro-α-methylbenzyl chloride was added. The mixture was stirred at 90° C. for 4 hours, and then cooled. Ice-water was added and the mixture was extracted with n-hexane. The n-hexane layer was washed with water and dried over anhydrous magnesium sulfate and the solvent was evaporated off. The residue obtained was purified by distillation under reduced pressure to afford 36 g of 2-fluoro-α-methylbenzyl cyanide, b.p.$_{0.5}$ 55° C.

(2) To 24 g of 2-fluoro-α-methylbenzyl cyanide was added dropwise 40 ml of fuming nitric acid while maintaining the temperature 0°–5° C. After addition, the mixture was gradually warmed up to room temperature, poured into ice-water and extracted with ether. The ether layer was washed with water and dried over anhydrous magnesium sulfate and the solvent was evaporated off. The crude crystals obtained were recrystallized from benzene—n-hexane to afford 25.8 g of 2-fluoro-α-methyl-5-nitrobenzyl cyanide, m.p. 55°–56° C.

(3) To 100 ml of aqueous 50% sulfuric acid was added 10 g of 2-fluoro-α-methyl-5-nitrobenzyl cyanide, followed by stirring at 80° C. for 6 hours. The mixture was cooled, 100 ml of a saturated brine was added, and the mixture was extracted with ether. The ether layer was washed with water and dried over anhydrous magnesium sulfate and the solvent was evaporated off. The crude crystals obtained were recrystallized from benzene—n-hexane to give 8.3 g of 2-(2-fluoro-5-nitrophenyl)propionic acid, m.p. 88°–90° C.

(4) In 50 ml of ethanol was dissolved 5 g of 2-(2-fluoro-5-nitrophenyl)propionic acid. To the solution was added 250 mg of 5% palladium on charcoal to conduct catalytic hydrogenation. After the reduction was completed, the mixture was filtered through Celite and the solvent was evaporated off to give 4.1 g of the crude crystals of 2-(5-amino-2-fluorophenyl)propionic acid, m.p. 146°–149° C.

(5) In 12 ml of 18% aqueous hydrochloric acid was dissolved 4 g of 2-(5-amino-2-fluorophenyl)propionic acid, and 4 ml of an aqueous solution of 1.1 g of sodium nitrite was added dropwise while maintaining the temperature between −15° C. and −10° C. The mixture was stirred for an hour, to which 40 ml of acetone, 8 g of 1,1-dichloroethylene, 1250 mg of sodium hydrogen carbonate and 400 mg of cupric chloride dihydrate were successively added. The mixture was gradually warmed up to room temperature and stirred overnight. The acetone layer was separated and the solvent was evaporated off. The residue was dissolved in ether, washed with water and dried over anhydrous magnesium sulfate. The solvent was evaporated off and the residue obtained was subjected to silica gel column chromatography (eluent: n-hexane—ethyl acetate=20:1) to afford 3.9 g of 2-[2-fluoro-5-(2,2,2-trichloroethyl)phenyl]propionic acid as an oily substance.

IR (neat) cm$^{-1}$: 1710 (COOH).

NMR (CDCl$_3$).

δ=1.53 (3H, d, J=8.0 Hz, CH$_3$); 3.89 (2H, s, CH$_2$); 4.08 (1H, q, J=8.0 Hz, >CHCO$_2$H); 7.07 (1H, t, J=9.0 Hz, Ar-H); 7.3–7.5 (2H, m, Ar-H×2).

(6) In 20 ml of dimethylformamide was dissolved 2 g of 2-[2-fluoro-5-(2,2,2-trichloroethyl)phenyl]propionic acid, and 2.3 g of anhydrous potassium carbonate was added. The mixture was stirred at 70° C. for 3 hours.

After cooling, the mixture was poured into ice-water, made acidic with hydrochloric acid and extracted with ether. The ether layer was washed with water and dried over anhydrous magnesium sulfate and the solvent was evaporated off. The residue obtained was subjected to silica gel column chromatography (eluent: n-hexane—ethyl acetate=10:1) and recrystallized from petroleum ether to afford 1.1 g of 2-[5-(2,2-dichlorovinyl)-2-fluorophenyl]propionic acid(ST-40), m.p. 80°–82° C.

EXAMPLE 12

To a mixture of 4.17 g of 2-[4-(2,2-dichlorovinyl)-phenyl]propionic acid(ST-1), 4.15 g of potassium carbonate and 60 ml of acetone was added dropwise 2.98 g of prenyl bromide with stirring, and the whole was refluxed for 5 hours. After cooling, the solvent was evaporated off under reduced pressure, water was added and the mixture was extracted with n-hexane. The n-hexane layer was washed with water, dried over anhydrous magnesium sulfate and concentrated. The residue was distilled under reduced pressure to give 4.2 g of prenyl 2-[4-(2,2-dichlorovinyl)phenyl]propionate(ST-41) as an oily substance, b.p. 135°–137° C./0.01 mmHg.

The following compounds were obtained from the corresponding materials by procedures similar to that of Example 12.

Isopentyl 2-[4-(2,2-dichlorovinyl)phenyl]propionate(ST-42), b.p. 124° C./0.09 mmHg.

Methoxymethyl 2-[4-(2,2-dichlorovinyl)phenyl]propionate (ST-43), b.p. 127° C./0.1 mmHg.

2-Pyridylmethyl 2-[4-(2,2-dichlorovinyl)phenyl]propionate (ST-44), b.p. 176° C./0.09 mmHg.

1-(Acetoxy)ethyl 2-[4-(2,2-dichlorovinyl)phenyl]propionate(ST-45), b.p. 145° C./0.3 mmHg.

Propionyloxymethyl 2-[4-(2,2-dichlorovinyl)phenyl]-propionate(ST-46), b.p. 146° C./0.07 mmHg.

1-(Propionyloxy)ethyl 2-[4-(2,2-dichlorovinyl)-phenyl]propionate(ST-47), b.p. 158° C./0.25 mmHg.

1-(Palmitoyloxy)ethyl 2-[4-(2,2-dichlorovinyl)-phenyl]propionate(ST-48), m.p. 34°–37° C.

2-Phthalidyl 2-[4-(2,2-dichlorovinyl)phenyl]propionate(ST-49), m.p. 82°–96° C.

Prenyl 2-[4-(2,2-dichlorovinyl)-3-fluorophenyl]propionate (ST-50), b.p. 126°–128° C./0.15 mmHg.

Methoxymethyl 2-[4-(2,2-dichlorovinyl)-3-fluorophenyl]-propionate (ST-51), b.p. 112°–114° C./0.08 mmHg.

Methoxymethyl 4-(2,2-dichlorovinyl)-phenylacetate(ST-52),

Prenyl 4-(2,2-dichlorovinyl)phenylacetate(ST-53), 1-(Acetoxy)ethyl 3-(2,2-dichlorovinyl)-phenylacetate(ST-54), b.p. 155°–156° C./0.6 mmHg.

EXAMPLE 13

To a solution of 1.2 g of 2-[4-(2,2-dichlorovinyl)-3-fluorophenyl]propionic acid(ST-8) in 50 ml of ethanol was added 0.3 ml of conc. sulfuric acid, and the mixture was refluxed for 3 hours. After cooling, the solvent was evaporated off, the ice-water was added and the mixture was extracted with n-hexane. The n-hexane layer was washed with water, dried over anhydrous magnesium sulfate and concentrated. The residue was distilled under reduced pressure to afford 0.77 g of ethyl 2-[4-(2,2-dichlorovinyl)-3-fluorophenyl]propionate(ST-55) as an oily substance, b.p. 108°–110° C./0.15 mmHg.

The following compounds were obtained from the corresponding materials by procedures similar to that of Example 13.

Ethyl 2-[4-(2,2-dichlorovinyl)phenyl]propionate(ST-5), b.p. 128°–129° C./0.2 mmHg.

Ethyl 2-[3-chloro-4-(2,2-dichlorovinyl)phenyl]propionate (ST-56), b.p. 124°–126° C./0.22 mmHg.

Ethyl 4-(2,2-dichlorovinyl)phenylacetate(ST-57),

Ethyl 2-[4-(2,2-difluorovinyl)phenyl]propionate(ST-6).

EXAMPLE 14

To a solution of 2.62 g of thionyl chloride in 30 ml of benzene was added dropwise a mixture of 4.9 g of 2-[4-(2,2-dichlorovinyl)phenyl]propionic acid(ST-1), 1.74 g of pyridine and 25 ml of benzene with stirring at 3°–5° C. The reaction mixture was stirred at room temperature for 2 hours and extracted with n-hexane. The n-hexane layer was washed with water, dried over anhydrous magnesium sulfate and evaporated off. The residue was added dropwise to a mixture of 4.63 g of geraniol, 15 ml of dimethylformamide, 2 ml of pyridine and 30 ml of benzene with stirring at 3°–5° C. The whole was stirred at 5°–10° C. for 2 hours, and extracted with n-hexane. The n-hexane layer was washed with water, dried over anhydrous magnesium sulfate and evaporated off. The residue was subjected to silica gel column chromatography (eluent: n-hexane—dichloromethane=5:1) to give 6.0 g of geranyl 2-[4-(2,2-dichlorovinyl)phenyl]propionate(ST-58) as an oily substance.

The following compounds were obtained from the corresponding materials by procedures similar to that of Example 14.

2-Hydroxyethyl 2-[4-(2,2-dichlorovinyl)phenyl]propionate (ST-59), b.p. 149° C./0.07 mmHg.

Farnesyl 2-[4-(2,2-dichlorovinyl)phenyl]propionate(ST-60).

Cyclohexyl 2-[4-(2,2-dichlorovinyl)phenyl]propionate(ST-61), b.p. 149° C./0.05 mmHg.

Geranyl 2-[3-chloro-4-(2,2-dichlorovinyl)phenyl]-propionate(ST-62),

Farnesyl 3-(2,2-dichlorovinyl)phenylacetate(ST-63).

We claim:

1. A compound of the general formula

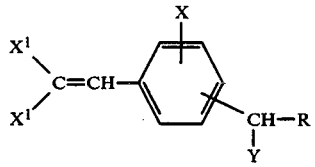

wherein X is hydrogen or halogen, $X^1$ is halogen, R is hydrogen or methyl, Y is hydroxymethyl, carboxyl, —$COOR^1$ or —$COR^2$ wherein $R^1$ is prenyl, geranyl, farnesyl, cyclohexyl, phthalidyl, straight or branched chain alkyl having 1 to 6 carbon atoms, or said alkyl substituted with hydroxy, methoxy, pyridyl or alkanoyloxy having 2 to 16 carbon atoms, and $R^2$ is amino, hydroxyamino, mono-(or di-)alkylamino in which the alkyl moiety contains 1 or 2 carbon atoms, ethoxycarbonylmethylamino, carboxymethylamino, thiazolylamino, cyclohexylamino, pyridylamino, morpholino, N-methylpiperazino, phenylamino, phenylamino substituted with one or two of halogen, hydroxy, methyl, methoxy, trifluoromethyl or carboxyl at the phenyl ring, and the pharmaceutically acceptable salts thereof when Y is carboxyl.

2. A compound according to claim 1 wherein X is hydrogen $X^1$ is chlorine, R is methyl and Y is carboxyl.

3. A compound according to claim 1 wherein X is halogen, $X^1$ is chlorine, R is methyl and Y is carboxyl.

4. 2-[4-(2,2-Dichlorovinyl)phenyl]propionic acid 5. 2-[4-(2,2-Dichlorovinyl)-3-fluorophenyl]propionic acid 6. Aluminum 2-[4-(2,2-dichlorovinyl)phenyl]propionate.